United States Patent
Fieber et al.

(10) Patent No.: US 11,504,310 B2
(45) Date of Patent: Nov. 22, 2022

(54) AQUEOUS MICROEMULSION

(71) Applicant: Firmenich SA, Geneva (CH)

(72) Inventors: Wolfgang Fieber, Geneva (CH); Barbara Buchs, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/617,272

(22) PCT Filed: May 24, 2018

(86) PCT No.: PCT/EP2018/063634
§ 371 (c)(1),
(2) Date: Nov. 26, 2019

(87) PCT Pub. No.: WO2018/219770
PCT Pub. Date: Dec. 6, 2018

(65) Prior Publication Data
US 2020/0306152 A1    Oct. 1, 2020

(30) Foreign Application Priority Data
Jun. 1, 2017 (EP) .................... 17174036

(51) Int. Cl.
| | | |
|---|---|---|
| *A61K 8/06* | (2006.01) | |
| *A61K 8/34* | (2006.01) | |
| *A61K 8/39* | (2006.01) | |
| *A61K 8/86* | (2006.01) | |
| *A61K 8/92* | (2006.01) | |
| *A61Q 13/00* | (2006.01) | |

(52) U.S. Cl.
CPC .............. *A61K 8/068* (2013.01); *A61K 8/062* (2013.01); *A61K 8/342* (2013.01); *A61K 8/39* (2013.01); *A61K 8/86* (2013.01); *A61K 8/922* (2013.01); *A61Q 13/00* (2013.01); *A61K 2800/30* (2013.01)

(58) Field of Classification Search
CPC ........ A61K 8/068; A61K 8/062; A61K 8/342; A61K 8/39; A61K 8/86; A61K 8/922; A61K 2800/30; A61K 2800/596; A61Q 13/00; A61L 9/012
See application file for complete search history.

(56) References Cited

U.S. PATENT DOCUMENTS

| | | | |
|---|---|---|---|
| 5,374,614 A | 12/1994 | Behan et al. | |
| 2007/0202063 A1 | 8/2007 | Dihora et al. | |
| 2009/0202446 A1* | 8/2009 | Vlad ................. | A61L 9/012 424/45 |
| 2009/0311195 A1* | 12/2009 | Clark .................. | A01N 25/30 424/45 |

FOREIGN PATENT DOCUMENTS

| | | | | |
|---|---|---|---|---|
| EP | 0571677 A1 * | 12/1993 | ............ | A61K 8/062 |
| EP | 0572080 A1 | 12/1993 | | |
| EP | 1741775 A1 | 1/2007 | | |
| GB | 2432843 A | 6/2007 | | |
| GB | 2432850 A | 6/2007 | | |
| GB | 2432851 A | 6/2007 | | |
| GB | 2432852 A | 6/2007 | | |
| JP | H0640877 A | 2/1994 | | |
| JP | 2008-517051 A | 5/2008 | | |
| WO | 9850011 A1 | 11/1998 | | |
| WO | 2005054422 A1 | 6/2005 | | |
| WO | 2006043177 A1 | 4/2006 | | |
| WO | 2007062733 A1 | 6/2007 | | |
| WO | 2007062833 A1 | 6/2007 | | |
| WO | 2008016684 A1 | 2/2008 | | |
| WO | 009125441 A1 | 10/2009 | | |
| WO | 2012084904 A1 | 6/2012 | | |
| WO | 2013174615 A2 | 11/2013 | | |

OTHER PUBLICATIONS

International Search Report and Written Opinion for International Application No. PCT/EP2018/063634, dated Jul. 2, 2018. 14 pages.
Asgharian et al., "Synthesis and Performance of High Efficiency Cosurfactants: 2. Commercial Variants", Journal of Dispersion Science and Technology, Published 1992, pp. 515-525, vol. 13, No. 5.
Sensient Cosmetic Technologies, "Solubilisant LRI: Technical Bulletin", Sensient Cosmetic Technologies lcw, Published Apr. 1, 2003, p. 1.

* cited by examiner

*Primary Examiner* — Isaac Shomer
*Assistant Examiner* — Amanda Michelle Petritsch

(57) ABSTRACT

The present invention relates to a stable and clear microemulsion comprising:
   an oil phase comprising an hydrophobic active ingredient;
   an aqueous phase; and
   a surfactant system comprising:
      a non-ionic primary surfactant system;
      a first non-ionic co-surfactant system, and
      a second non-ionic co-surfactant system.

19 Claims, No Drawings

AQUEOUS MICROEMULSION

CROSS-REFERENCE TO RELATED APPLICATIONS

This application is a U.S. National Phase Application of PCT/EP2018/063634, filed on May 24, 2018, which claims the benefit of priority to European Patent Application Number 17174036.8, filed Jun. 1, 2017, the entire contents of which are hereby incorporated by reference herein.

TECHNICAL FIELD

The present invention relates to an aqueous microemulsion comprising a non-ionic surfactant system. More particularly, the surfactant system comprises at least one non-ionic primary surfactant system, at least a first non-ionic co-surfactant system, and at least a second non-ionic co-surfactant system.

Perfuming compositions and consumer products comprising said microemulsion, in particular perfumed consumer products in the form of home care or personal care products, are also part of the invention.

BACKGROUND OF THE INVENTION

Microemulsions are liquid dispersions of water and oil that are generally made homogeneous, transparent and stable by the addition of relatively large amounts of surfactants. Water-based consumer products in home-care such as all-purpose cleaners, shampoo, shower gels, aerosols or ethanol-free products in body- and personal care are typically oil in water microemulsions, where the dispersed oil phase contains apolar actives such as perfumes. As opposed to emulsions, which are metastable systems and will eventually phase separate upon long term storage, microemulsions form spontaneously and are thermodynamically stable. Microemulsions are very sensitive to composition and temperature, and the formulation of microemulsions requires the finding of the right balance between the main components water, oil, surfactant and optionally additional additives. In particular, a match between oil phase and surfactant polarity is crucial for the formation of microemulsions with optimal compositions allowing the solubilization of high amounts of oil. The addition of co-surfactants and water-miscible co-solvents helps to increase the stability range in terms of temperature and solubilization capacity, making such microemulsions well balanced and stable colloidal systems.

Now, for the purpose of the present invention, for perfumery industry for example, it is not desirable to incorporate an important amount of surfactant relative to the amount of fragrance (hydrophobic active ingredient). Using high amounts of surfactant is not desirable from a sustainability standpoint of view. Adding less material decreases the organic chemical content in waste water. It also contributes to lower the cost of the final product. Moreover, for particular applications such as aerosols, lower amounts of surfactant decrease the content of non-volatile ingredients and in consequence solid fall-out after spray application is reduced. And finally, lower amounts of surfactants can reduce irritancy on skin or in the lung upon inhalation when used in body or personal care products or aerosol sprays.

In particular, skin irritancy is first and foremost a function of surfactant polarity and charge. It is known that the most irritant for skin are cationic surfactants, followed by anionics, non-ionic and amphoterics.

Furthermore, in the industrial development of a microemulsion, it is very important that a formulation can be utilized in a variety of different categories and application products. One basic parameter that differs is the amount of the oil phase (perfume for example) used in the different applications.

Microemulsions have been widely described in the prior art. For example EP0571677 and U.S. Pat. No. 5,374,614 disclose aqueous perfume oil microemulsions comprising a surfactant system consisting of primary surfactant and co-surfactant(s).

Even if microemulsions are well-known in the art, stability properties of these microemulsions could be improved.

Therefore, there is a need to provide a microemulsion that would be stable within a wide oil phase concentration and would be therefore suitable for different applications.

SUMMARY OF THE INVENTION

The present invention discloses that a microemulsion comprising a low amount of surfactants can be obtained together with the transparency, fluidity and stability requirements by using a specific combination between primary surfactant(s) and co-surfactant(s).

Therefore, a first object of the present invention is a microemulsion comprising:
  an oil phase comprising a hydrophobic active ingredient, preferably a perfume;
  an aqueous phase; and
  a surfactant system comprising:
    a non-ionic primary surfactant system;
    a first non-ionic co-surfactant system, and
    a second non-ionic co-surfactant system;
  characterized in that:
  the non-ionic primary surfactant system comprises at least one ethoxylated alcohol having between 5 and 19 PEG units;
  the first non-ionic co-surfactant system comprises a PEG-modified hydrogenated castor oil having more than 19 PEG units and a polypropoxylated-polyethoxylated alcohol; and
  the second non-ionic co-surfactant system is selected from the group consisting of ethoxylated alcohols having more than 19 PEG units, a PEG-modified hydrogenated castor oil having more than 19 PEG and mixtures thereof.

A second object of the present invention is a perfuming composition comprising a microemulsion as defined in the present invention, at least one ingredient selected from the group consisting of perfuming co-ingredients, a perfumery carrier and mixtures thereof, and optionally at least one perfumery adjuvant.

A third and a fourth object of the present invention describe a consumer product comprising the microemulsion or the perfuming composition as defined in the present invention.

Finally, a last object of the invention consists of the use of a surfactant system comprising at least one non-ionic primary surfactant system, at least a first non-ionic co-surfactant system, and at least a second non-ionic co-surfactant system to stabilize a microemulsion comprising an oil phase and an aqueous phase;
  characterized in that:
  the non-ionic primary surfactant system comprises at least one ethoxylated alcohol having between 5 and 19 PEG units;

the first non-ionic co-surfactant system comprises a PEG-modified hydrogenated castor oil having more than 19 PEG units and a polypropoxylated-polyethoxylated alcohol, and the second non-ionic co-surfactant system is selected from the group consisting of ethoxylated alcohols having more than 19 PEG units, a PEG-modified hydrogenated castor oil having more than 19 PEG and mixtures thereof.

DETAILED DESCRIPTION OF THE INVENTION

Due to a synergetic effect within the surfactant system, the microemulsion of the invention includes a low amount of surfactants and is in the form of a stable and transparent oil dispersion over a large temperature ranges regardless the concentration of the oil phase (perfume oil for example) in the microemulsion.

A first object of the present invention is therefore a microemulsion comprising:
  an oil phase comprising a hydrophobic active ingredient, preferably a perfume;
  an aqueous phase; and
  a surfactant system comprising:
    a non-ionic primary surfactant system;
    a first non-ionic co-surfactant system, and
    a second non-ionic co-surfactant system;
  characterized in that:
  the non-ionic primary surfactant system comprises at least one ethoxylated alcohol having between 5 and 19 PEG units;
  the first non-ionic co-surfactant system comprises a PEG-modified hydrogenated castor oil having more than 19 PEG units and a polypropoxylated-polyethoxylated alcohol; and
  the second non-ionic co-surfactant system is selected from the group consisting of ethoxylated alcohols having more than 19 PEG units, a PEG-modified hydrogenated castor oil having more than 19 PEG and mixtures thereof.

According to the invention, the terms "PEG-modified hydrogenated castor oil having more than 19 PEG" and "modified hydrogenated castor oil having more than 19 PEG" are used indifferently.

By «PEG-modified hydrogenated castor oil» it is meant a compound obtained by reacting 1 mole of hydrogenated castor oil with n moles of ethylene oxide. According to the invention, n is greater than 19, preferably comprised between 20 and 60, more preferably is 30, 40 or 60.

By "microemulsion", it should be understood that it is a liquid dispersion of water and oil that are formed spontaneously when oil, water, surfactants and co-surfactants and optionally co-solvents are mixed together. Microemulsion droplets have a narrow droplet size distribution with a mean diameter range typically below 100 nm.

It has been shown that microemulsions according to the invention are transparent at room temperature (RT) and are stable within a large temperature range (typically RT±10-20° C.).

The term transparent means that the microemulsions in the absence of coloring or fluorescent agents have transmittance values in the visible light (500-800 nm) of 100% at a path length of 1 cm referenced against demineralized water.

Surfactant System

The surfactant system of the present invention comprises:
  a non-ionic primary surfactant system;
  a first non-ionic co-surfactant system, and
  a second non-ionic co-surfactant system.

According to the invention, it should be understood that the primary surfactant system and/or the first co-surfactant system and/or the first co-surfactant system can be an aqueous blend of non-ionic surfactants.

Non-Ionic Primary Surfactant

According to the invention, the non-ionic primary surfactant has to be compatible with the hydrophobic active ingredient. In particular, to create highly performing microemulsions in terms of solubilization capacity and temperature stability, the oil polarity should match the polarity of the surfactant used. Thus, depending on the nature of the hydrophobic active ingredient, the person skilled in the art will be able to select a suitable primary surfactant notably according its HLB (hydrophilic lipophilic balance) which is a well-known parameter.

According to an embodiment, the non-ionic primary surfactant has an HLB between 9 and 18, preferably between 10 and 15

According to an embodiment, the alkyl group of the ethoxylated alcohol of the non-ionic primary surfactant system is chosen in the group consisting of linear, branched, primary, and secondary alcohols with a chain length containing a total number of carbon atoms between 8 and 18.

Typically, the non-ionic primary surfactant is chosen in the group consisting of PEG(7), PEG(9), PEG(12) secondary alcohol ethoxylate and mixtures thereof.

According to an embodiment, the non-ionic primary surfactant system comprises two or three non-ionic primary surfactants, preferably chosen in the group consisting of PEG(7), PEG(9), PEG(12) secondary alcohol ethoxylate.

Preferably, the microemulsion comprises between 0.05 to 30% by weight of the primary surfactant system based on the total weight of the microemulsion.

Non-Ionic Co-Surfactant Systems

According to the invention, in addition to the primary surfactant, the surfactant system comprises two co-surfactant systems, namely a first co-surfactant system and a second co-surfactant system.

The use of co-surfactant(s) in the surfactant system improves the temperature stability of the microemulsions by enlarging the zone of transparent microemulsions in the temperature-perfume concentration phase diagram.

Preferably, the microemulsion comprises between 0.05 to 30% by weight of co-surfactant systems based on the total weight of the microemulsion.

First Non-Ionic Co-Surfactant System

According to the invention, the first non-ionic co-surfactant system comprises a PEG-modified hydrogenated castor oil having more than 19 PEG units and a polypropoxylated polyethoxylated alcohol.

According to an embodiment, the PEG-modified hydrogenated castor oil present in the first co-surfactant system is a PEG-modified hydrogenated castor oil having between 20 and 60 PEG units.

According to another embodiment, the polypropoxylated-polyethoxylated alcohol present in the first co-surfactant system is a butyl alcohol ether.

According to a particular embodiment, the first co-surfactant system comprises PPG-26 Buteth-26 and PEG-modified hydrogenated castor oil having 40 PEG units.

According to another embodiment, the first co-surfactant comprises and preferably consists of a mixture consisting of PPG-26 Buteth-26, PEG-modified hydrogenated castor oil having 40 PEG units and water. Said mixture is commercially available and well-known under the trademark Solubilizer LRI® (origin: LCW Sensient Cosmetic Technologies).

Second Non-Ionic Co-Surfactant System

According to the invention, the second co-surfactant system comprises at least one non-ionic surfactant selected from the group consisting of ethoxylated alcohols having more than 19 PEG units or a second PEG-modified hydrogenated castor oil having more than 19 PEG and mixtures thereof.

According to an embodiment, the second co-surfactant is an ethoxylated alcohol having between 20 and 60 PEG units.

The alkyl group of the ethoxylated alcohol of the second co-surfactant is preferably chosen in the group consisting of linear, branched, primary, and secondary alcohols with a chain length containing a total number of carbon atoms between 8 and 18.

According to an embodiment, the ethoxylated alcohol has an HLB between 14 and 18.

Typically, the second co-surfactant is chosen in the group consisting of PEG(20), PEG-30 or PEG-40 secondary alcohol ethoxylate, and mixtures thereof.

According to another embodiment, the second co-surfactant is a PEG-modified hydrogenated castor oil having preferably between 20 and 60 PEG units.

According to a particular embodiment, the second co-surfactant is a PEG-modified hydrogenated castor oil having 30 PEG units, 40 PEG units, 60 PEG units, and mixtures thereof.

According to an embodiment, the PEG-modified hydrogenated castor oil having more than 19 PEG units comprised in the first co-surfactant system and the PEG-modified hydrogenated castor oil having more than 19 PEG units comprised in the second co-surfactant system are different.

What is meant by "different PEG-modified hydrogenated castor oil" is PEG-modified hydrogenated castor oil differing in polarity as a function of different lengths of the PEG chain.

According to another particular embodiment, the surfactant system comprises, preferably consists of Solubilizer LRI and a PEG(40) modified hydrogenated castor oil as second co-surfactant.

As an example, PEG(40) modified hydrogenated castor oil is commercially available and well-known under the trademark Cremophor RH40 (Origin: BASF).

According to a particular embodiment:
the first co-surfactant system comprises PPG-26 Buteth-26 and a PEG-modified hydrogenated castor oil having 40 PEG units, and
the second co-surfactant system comprises a non-ionic surfactant chosen in the group consisting of a PEG-modified hydrogenated castor oil having 30 PEG units, 40 PEG units, 60 PEG units, and mixtures thereof.

According to an embodiment, the weight ratio between primary surfactant system and co-surfactant systems is from 5:95 to 95:5, more preferably from 20:80 to 80:20, even more preferably from 40:60 to 60:40. In one particular embodiment the ratio is 50:50.

According to an embodiment, the weight ratio between the second co-surfactant system and the first co-surfactant system is from 5:95 to 95:5. In one particular embodiment the preferred ratio is from 40:60 to 60:40. In another embodiment the ratio is 90:10.

As mentioned previously, the microemulsion of the invention has a low amount of surfactants and forms a stable and transparent solution even when the microemulsion has a high concentration of the oil phase (such as a perfume).

Therefore, according to an embodiment, the weight ratio Rw between the hydrophobic active ingredient and the surfactant system satisfies the following equation: $0.7 \leq Rw \leq 2$, preferably $1 \leq Rw \leq 2$.

According to particular embodiment, the surfactant system consists of:
at least a non-ionic primary surfactant,
at least a first non-ionic co-surfactant, and
at least a second non-ionic co-surfactant.

Optional Additional Surfactants

According to an embodiment, the surfactant system further comprises at least one surfactant chosen in the group consisting of cationic surfactant, anionic surfactant, amphoteric surfactant and mixtures thereof.

According to a particular embodiment, the surfactant system comprises an amphoteric surfactant.

Non limiting examples of amphoteric surfactant include alkyl betaines, alkyl sulfobetaines, alkyl amine oxides, lecithin (phospholipids) such as phosphatidylcholine, and mixtures thereof.

This embodiment is particularly suitable when the concentration of the oil phase is about 10%.

According to a particular embodiment, the amphoteric surfactant is lecithin.

According to a particular embodiment, the surfactant system comprises, preferably consists of:
at least a non-ionic primary surfactant,
at least a first non-ionic co-surfactant,
at least a second non-ionic co-surfactant, and
at least one amphoteric surfactant.

Non limiting examples of cationic surfactant include quarternary ammonium compounds, benzalkonium chlorides, and mixtures thereof.

Non limiting examples of anionic surfactant include alkyl sulfates, alkyl ether sulfates, alkyl sulfonates, aryl sulfonates, isethionates, mono or dialkyl sulfosuccinates, alkyl amphoacetates, acyl amino acid derivatives such as taurates, sarcosinates, glycinates, alaninates, glutamates, alkyl carboxylates, and mixtures thereof.

According to an embodiment, the surfactant system is free from a cationic surfactant and/or an ionic surfactant.

According to an embodiment, the surfactant system is free from a cationic surfactant and/or an anionic surfactant.

Organic Co-Solvent(s)

According to an embodiment, the microemulsion further comprises a water miscible organic co-solvent, preferably chosen in the group consisting of mono- and polyhydric solvents to further stabilize the microemulsions. Non limiting examples of such solvents can be found from the group containing ethanol, propanol, propylene glycol, hexylene glycol, dipropylene glycol, glycerol, di-isoproylidene glycol, butylene glycol (1,3-butanediol) and isopropanol, and mixtures thereof Oil Phase Comprising a Hydrophobic Active Ingredient By "hydrophobic active ingredient", it is meant any active ingredient—single ingredient or a mixture of ingredients—which forms a two-phases dispersion when mixed with water.

Hydrophobic active ingredients are preferably chosen from the group consisting of flavor, flavor ingredients, perfume, perfume ingredients, nutraceuticals, cosmetics, insect control agents, biocide actives and mixtures thereof.

The nature and type of the insect control agents present in the hydrophobic internal phase do not warrant a more detailed description here, which in any case would not be exhaustive, the skilled person being able to select them on the basis of its general knowledge and according to intended use or application.

Examples of such insect control agents are birch, DEET (N,N-diethyl-m-toluamide), essential oil of the lemon *eucalyptus* (Corymbia *citriodora*) and its active compound p-menthane-3,8-diol (PMD), icaridin (hydroxyethyl isobutyl piperidine carboxylate), Nepelactone, Citronella oil, Neem oil, Bog Myrtle (*Myrica* Gale), Dimethyl carbate, Tricyclodecenyl allyl ether, IR3535 (3-[N-Butyl-N-acetyl]-aminopropionic acid, ethyl ester, Ethylhexanediol, Dimethyl phthalate, Metofluthrin, Indalone, SS220, anthranilate-based insect repellents, and mixtures thereof.

According to a particular embodiment, the hydrophobic-active ingredient comprises a mixture of a perfume with another ingredient selected from the group consisting of nutraceuticals, cosmetics, insect control agents and biocide actives.

According to a particular embodiment, the hydrophobic active ingredient comprises a perfume.

According to a particular embodiment, the hydrophobic active ingredient consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odor. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodor counteraction, antimicrobial effect, microbial stability, insect control.

The nature and type of the perfuming ingredients present in the hydrophobic internal phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

According to an embodiment, the oil phase concentration is comprised between 0.5 and 40%, preferably between 10 and 30%, more preferably between 15 and 30% by weight of the microemulsion.

The invention's compositions can be prepared according to any method known in the art.

A suitable method consists in adding successively the primary surfactants, the co-surfactants, the hydrophobic active ingredient and the co-solvent and in mixing homogeneously said components. Water is then added under stirring to obtain the desired concentrations.

Following the above method of preparation, stable, transparent clear microemulsions with a high oil content can be prepared by employing a minimum amount of surfactant.

Perfuming Composition

Another object of the invention is a perfuming composition comprising a microemulsion, at least one ingredient selected from the group consisting of perfuming co-ingredients, a perfumery carrier and mixtures thereof, and optionally at least one perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Consumer Product

The invention's microcapsules can advantageously be used in different fields of perfumery, i.e. fine or functional perfumery.

Consequently, another object of the present invention is represented by a consumer product, preferably a perfuming consumer product comprising the microemulsion as defined above.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises a functional formulation, as well as optionally additional benefit agents, corresponding to the desired consumer product, e.g. a detergent or an air freshener, and an olfactive effective amount of at least one invention's compound.

The nature and type of the constituents of the perfumery consumer product do not warrant a more detailed description here, which in any case would not be exhaustive, the skilled person being able to select them on the basis of his general knowledge and according to the nature and the desired effect of said product. These formulations do not warrant a detailed description here which would in any case not be exhaustive. The person skilled in the art of formulating such consumer products is perfectly able to select the suitable components on the basis of his general knowledge and of the available literature.

In particular, examples of such formulations can be found in the patents and patent applications relative to such products, for example in WO2008/016684, US2007/0202063, WO2007/062833, WO2007/062733, WO2005/054422, EP1741775, GB2432843, GB2432850, GB2432851, GB2432852, WO 9850011, WO2013174615 or WO2012084904.

Non-limiting examples of suitable perfumery consumer product can be a perfume, such as a fine perfume, a body splash, a cologne or an after-shave lotion; a fabric care product, such as a liquid detergent, a fabric softener, a fabric refresher, an ironing water, or a bleach; a body-care product, such as a hair care product (e.g. a shampoo, hair conditioner, a coloring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, or a hygiene product); an air care product, such as an air freshener; or a home care product, such all-purpose cleaners, liquid dishwashing products, toilet cleaners or products for cleaning various surfaces, for example sprays & wipes intended for the treatment/refreshment of textiles or hard surfaces (floors, tiles, stone-floors, etc.).

The microemulsions of the present invention can be concentrated or diluted, i;e they may contain large amounts of water or, on the contrary large amounts of perfume.

According to an embodiment, the consumer product is in the form of a home cleaning product, a home fragrancing product, a pest control product or a shoe care product and comprises the microemulsion or the perfuming composition as defined in the present invention.

According to a particular embodiment, the consumer product is an air freshener. According to the previous embodiment, the microemulsion of the invention is in a form appropriate to be diffused into its surroundings via an air freshener device of this type.

According to another embodiment, the consumer product is in the form of a fine fragrance product, a personal care product, an oral care product, comprising the microemulsion as defined above.

Thus, depending on the application, the microemulsion may also comprise optional ingredients such as corrosion inhibitors, anti-oxidants, dyestuffs, bittering agents, UV inhibitors, preservatives, chelating agents and any other appropriate oil or water soluble ingredients, current in this type of device. Such optional ingredients will represent no more than 3% w/w, or even 2% w/w, the percentages being relative to the total weight of the composition.

Another object of the invention is a method for stabilizing a microemulsion comprising an oil phase and an aqueous phase, which comprises adding into said microemulsion a surfactant system comprising:
  a non-ionic primary surfactant system;
  a first non-ionic co-surfactant system, and
  a second non-ionic co-surfactant system;
  characterized in that:
  the non-ionic primary surfactant system comprises at least one ethoxylated alcohol having between 5 and 19 PEG units;
  the first non-ionic co-surfactant system comprises a PEG-modified hydrogenated castor oil having more than 19 PEG units and a polypropoxylated-polyethoxylated alcohol, and
  the second non-ionic co-surfactant system is selected from the group consisting of ethoxylated alcohols having more than 19 PEG units, a PEG-modified hydrogenated castor oil having more than 19 PEG and mixtures thereof.

Finally, a last object of the invention is the use of a surfactant system comprising:
  a non-ionic primary surfactant system;
  a first non-ionic co-surfactant system, and
  a second non-ionic co-surfactant system;
  to stabilize a microemulsion comprising an oil phase and an aqueous phase characterized in that:
  the non-ionic primary surfactant system comprises at least one ethoxylated alcohol having between 5 and 19 PEG units;
  the first non-ionic co-surfactant system comprises a PEG-modified hydrogenated castor oil having more than 19 PEG units and a polypropoxylated-polyethoxylated alcohol; and
  the second non-ionic co-surfactant system is selected from the group consisting of ethoxylated alcohols having more than 19 PEG units or a PEG-modified hydrogenated castor oil having more than 19 PEG and mixtures thereof.

The microemulsion of the invention has proven to be particularly and advantageously stable over a wide temperature range and over a wide oil phase concentration range.

The invention will now be further described by way of examples. It will be appreciated that the invention as claimed is not intended to be limited in any way by these examples.

EXAMPLES

Section I: Sample Preparation

Primary surfactant system, co-surfactant systems, hydrophobic active ingredient (fragrance oil) and organic co-solvent are added successively and are homogeneously mixed. Demineralized water is then added under stirring to obtain the desired concentrations. Samples are left to equilibrate at room temperature at least 24 h before the measurements.

Section II: Temperature Stability Measurements

The temperature stability of the microemulsions is monitored on a Crystalline PV device from Technobis, The Netherlands. The samples are transferred to transparent 5 mL glass vials equipped with a magnetic stir bar and an overhead stirrer. Cooling and heating cycles are applied individually for each sample. A first cooling step is applied from 20° C. to 3° C. at a cooling rate of −1° C./min, followed by a heating step to 60° C. at a heating rate of +1° C./min. Finally, a cooling step is performed from 60° C. to 3° C. with a cooling rate of −0.5° C./min. The turbidity of the sample is monitored by LED detectors and expressed as transmittance in %. The path length is about 1.4 cm. Transparency of samples is defined by a transmittance of 100% in the Crystalline PV device. Temperature limits are detected on the final cooling ramp when the signal passes from below 100% (not transparent) to 100% (transparent) transmission indicating the upper temperature limit of the transparent zone of the temperature phase diagram and when the signal passes from 100% to below 100%, indicating the lower temperature limit of the transparent zone of the temperature phase diagram.

Section III: Fragrance Used

The different fragrances used in the following examples were prepared by mixing the following main ingredients in the proportions indicated in tables 1-4 below.

TABLE 1

| Composition of fragrance F1 | | |
|---|---|---|
| Raw materials | logP | wt % |
| PHENYLETHYL ALCOHOL [1] | 1.36 | 26.7 |
| BENZYL ACETATE | 1.96 | 8 |
| FLOROL ® [2] | 2.16 | 16 |
| HEDIONE ® [3] | 2.98 | 13.3 |
| DIHYDROMYRCENOL PURE [4] | 3.47 | 2.7 |
| GERANIOL LJ [5] | 3.47 | 13.3 |
| CITRONELLOL BJ [6] | 3.91 | 2.7 |
| HELVETOLIDE ® [7] | 5.51 | 5.3 |
| ISO E SUPER [8] | 5.18 | 2.7 |
| HABANOLIDE ® [9] | 4.88 | 8 |
| MUSCENONE DELTA [10] | 5.75 | 1.3 |
| | 2.82 | 100 |

[1] 2-PHENYLETHANOL
[2] (+ −)-TETRAHYDRO-2-ISOBUTYL-4-METHYL-4(2H)-PYRANOL, Origin: Firmenich SA, Geneva, Switzerland
[3] methyl 2-((1RS,2RS)-3-oxo-2-pentylcyclopentyl)acetate, Origin: Firmenich SA, Geneva, Switzerland
[4] (+ −)-2,6-DIMETHYL-7-OCTEN-2-OL
[5] 3,7-DIMETHYL-2,6-OCTADIEN-1-OL
[6] (+ −)-3,7-DIMETHYL-6-OCTEN-1-OL
[7] (+)-(1S,1'R)-2-[1-(3',3'-DIMETHYL-1'-CYCLOHEXYL)ETHOXY]-2-METHYLPROPYL PROPANOATE, Origin: Firmenich SA, Geneva, Switzerland
[8] (+ −)-1-(OCTAHYDRO-2,3,8,8-TETRAMETHYL-2-NAPHTHALENYL)-1-ETHANONE, Origin, International Flavors & Fragrances, USA
[9] 1-OXA-12/13-CYCLOHEXADECEN-2-ONE
[10] (+ −)-(4E)-3-METHYL-4-CYCLOPENTADECEN-1-ONE

TABLE 2

| Composition of fragrance F2 | | |
|---|---|---|
| COMPONENT NAME | logP | wt % |
| BENZYL ACETATE | 1.96 | 21.7 |
| DIHYDROMYRCENOL PURE [1] | 3.47 | 21.7 |
| CORANOL [2] | 3.98 | 10.9 |
| NEOBUTENONE ® [3] | 4.45 | 0.1 |
| HELVETOLIDE ® [4] | 5.51 | 4.3 |
| ISO E SUPER [5] | 5.18 | 28.2 |
| AMBROX ® [6] | 4.76 | 2.2 |
| EXALTOLIDE ® [7] | 6.15 | 10.9 |
| | 4.10 | 100 |

[1] (+ −)-2,6-DIMETHYL-7-OCTEN-2-OL
[2] 4-CYCLOHEXYL-2-METHYL-2-BUTANOL
[3] 1-(5,5-dimethyl-1-cyclohexen-1-yl)-4-penten-1-one, Origin: Firmenich SA, Geneva, Switzerland
[4] (+)-(1S,1'R)-2-[1-(3',3'-DIMETHYL-1'-CYCLOHEXYL)ETHOXY]-2-METHYLPROPYL PROPANOATE Origin: Firmenich SA, Geneva, Switzerland
[5] (+ −)-1-(OCTAHYDRO-2,3,8,8-TETRAMETHYL-2-NAPHTHALENYL)-1-ETHANONE, Origin, International Flavors & Fragrances, USA
[6] (−)-(3aR,5aS,9aS,9bR)-3a,6,6,9a-tetramethyldodecahydronaphtho[2,1-b]furan, Origin: Firmenich SA, Geneva, Switzerland
[7] oxacyclohexadecan-2-one, Origin: Firmenich SA, Geneva, Switzerland

TABLE 3

| Composition of fragrance F3 | | |
|---|---|---|
| COMPONENT NAME | logP | wt % |
| (+ −)-ETHYL 2-METHYLPENTANOATE | 2.76 | 2 |
| CINNAMIC ALDEHYDE [1] | 1.9 | 7 |
| COUMARIN [2] | 1.39 | 2 |
| DIETHYL MALONATE | 0.96 | 5.5 |
| ETHYL 2 METHYLBUTYRATE [3] | 2.26 | 2 |
| ETHYL VANILLIN [4] | 1.58 | 2 |
| EUGENOL F [5] | 2.27 | 8 |
| FRUCTONE ® [6] | 1.3 | 22 |
| GAMMA HEXALACTONE [7] | 0.6 | 0.5 |
| METHYL CINNAMATE [8] | 2.62 | 1.5 |
| PHENYLPROPYL ALCOHOL [9] | 1.88 | 8 |
| (Z)-3-HEXENYL ACETATE | 2.61 | 0.5 |
| UNDECALACTONE GAMMA [10] | 3.06 | 5 |
| VANILLIN PERF [11] | 1.21 | 2 |
| VERDOX™ [12] | 4.42 | 32 |
| | 2.61 | 100 |

[1] (E)-3-PHENYL-2-PROPENAL
[2] 2-CHROMENONE
[3] (+ −)-ethyl 2-methylbutanoate
[4] 3-ethoxy-4-hydroxybenzaldehyde
[5] 2-methoxy-4-(2-propen-1-yl)phenol
[6] ETHYL 2-METHYL-1,3-DIOXOLANE-2-ACETATE, Origin, International Flavors & Fragrances, USA
[7] (+ −)-4-HEXANOLIDE
[8] METHYL (E)-3-PHENYL-2-PROPENOATE
[9] 3-PHENYL-1-PROPANOL
[10] (+ −)-4-UNDECANOLIDE
[11] vanillin
[12] (+ −)-2-TERT-BUTYL-1-CYCLOHEXYL ACETATE, Origin, International Flavors & Fragrances, USA

TABLE 4

| Composition of fragrance F4 | | |
|---|---|---|
| COMPONENT NAME | logP | wt % |
| ALLYL AMYL GLYCOLATE [1] | 2.34 | 0.3 |
| AMYL ACETATE [2] | 2.26 | 2.5 |
| ANISALDEHYDE SPECIAL REDIST [3] | 1.76 | 0.8 |
| BENZYL ACETATE | 1.96 | 16.6 |
| CALONE ® [4] | 2.43 | 0.3 |
| CITRONELLOL BJ [5] | 3.91 | 1.7 |
| CORPS PRALINE [6] | 0.09 | 0.002 |
| DECALACTONE CP [7] | 2.72 | 1.7 |

TABLE 4-continued

Composition of fragrance F4

| COMPONENT NAME | logP | wt % |
|---|---|---|
| DIHYDROMYRCENOL PURE [8] | 3.47 | 5.8 |
| DIPROPYLENE GLYCOL | −0.67 | 0.2 |
| ETHYL 2 METHYLBUTYRATE [9] | 2.26 | 2.7 |
| ETHYL LINALOL [10] | 3.87 | 3.3 |
| FLOROL NE ® [11] | 2.16 | 8.9 |
| FRUCTONE ® [12] | 1.3 | 6.7 |
| HEDIONE ® [13] | 2.98 | 0.04 |
| HEXYL ACETATE | 2.83 | 5.0 |
| ISOCYCLOCITRAL [14] | 3.27 | 1.7 |
| ISORALDEINE 70 P [15] | 4.84 | 1.7 |
| ISOSPIRENE [16] | 4.54 | 0.0 |
| LINALOL BJ [17] | 2.97 | 6.7 |
| MOUSSE CRISTAL [18] | 3.22 | 0.0008 |
| NEOBUTENONE ALPHA ® [19] | 4.45 | 0.0003 |
| NONALACTONE GAMMA [20] | 2.08 | 3.3 |
| (2RS,4SR)-2-methyl-4-propyl-1,3-oxathiane | 2.35 | 0.004 |
| PHENYLETHYL ALCOHOL [21] | 1.36 | 5.0 |
| PINENE MIXTURE [22] | 4.44 | 0.04 |
| (Z)-3-HEXEN-1-OL | 1.61 | 0.0001 |
| RHUBOFIX [22] | 3.85 | 0.004 |
| ROSE OXIDE [24] | 3.58 | 0.0004 |
| UNDECALACTONE GAMMA [25] | 3.06 | 1.7 |
| VELOUTONE [26] | 4.34 | 0.004 |
| VERDOX ™ [27] | 4.42 | 6.7 |
| VERDYL PROPIONATE [28] | 3.34 | 16.6 |
| (1RS,2RS)-2,4-dimethyl-3-cyclohexene-1-carbaldehyde | 2.85 | 0.004 |
| | 2.71 | 100 |

[1] ALLYL (2/3-METHYLBUTOXY)ACETATE
[2] 2/3-METHYLBUTYL ACETATE
[3] 4-METHOXYBENZALDEHYDE
[4] 7-methyl-2H-1,5-benzodioxepin-3(4H)-one, Origin: Firmenich SA, Geneva, Switzerland
[5] (+ −)-3,7-DIMETHYL-6-OCTEN-1-OL
[6] 3-HYDROXY-2-METHYL-4(4H)-PYRANONE
[7] (+ −)-4-DECANOLIDE
[8] (+ −)-2,6-DIMETHYL-7-OCTEN-2-OL
[9] (+ −)-ethyl 2-methylbutanoate
[10] (E/Z)-3,7-DIMETHYL-1,6-NONADIEN-3-OL
[11] (+ −)-TETRAHYDRO-2-ISOBUTYL-4-METHYL-4(2H)-PYRANOL, Origin: Firmenich SA, Geneva, Switzerland
[12] ETHYL 2-METHYL-1,3-DIOXOLANE-2-ACETATE, Origin: Firmenich SA, Geneva, Switzerland
[13] methyl 2-((1RS,2RS)-3-oxo-2-pentylcyclopentyl)acetate, Origin: Firmenich SA, Geneva, Switzerland
[14] TRIMETHYL-3-CYCLOHEXENE-1-CARBALDEHYDE
[15] (+ −)-(3E)-3-methyl-4-(2,6,6-trimethyl-2-cyclohexen-1-yl)-3-buten-2-one
[16] (5RS,9SR,10RS)-2,6,9,10-TETRAMETHYL-1-OXASPIRO[4.5]DECA-3,6-DIENE
[17] (+ −)-3,7-DIMETHYL-1,6-OCTADIEN-3-OL
[18] METHYL 2,4-DIHYDROXY-3,6-DIMETHYLBENZOATE
[19] 1-(5,5-dimethyl-1-cyclohexen-1-yl)-4-penten-1-one, Origin: Firmenich SA, Geneva, Switzerland
[20] (+ −)-4-NONANOLIDE
[21] 2-PHENYLETHANOL
[22] alpha/beta pinene
[23] (+ −)-3,4'-dimethylspiro[oxirane-2,9'-tricyclo[6.2.1.0~2,7~]undec[4]ene
[24] TETRAHYDRO-4-METHYL-2-(2-METHYL-1-PROPENYL)-2H-PYRAN
[25] (+ −)-4-UNDECANOLIDE
[26] (+ −)-2,2,5-trimethyl-5-pentylcyclopentanone
[27] (+ −)-2-TERT-BUTYL-1-CYCLOHEXYL ACETATE, Origin: International Flavors & Fragrances, USA
[28] TRICYCLO[5.2.1.0(2,6)]DEC-3-EN-8-YL PROPANOATE

Example 1

Preparation of Microemulsions According to the Invention

Microemulsions according to the invention were prepared according to the protocol defined in section I using:

- different primary surfactant mixtures
- different co-solvent mixtures
- different fragrances, and
- different fragrance load.

Upper and lower temperature limit were determined using the experimental protocol defined in section II.

Results are summarized in tables 5 and 6 below.

TABLE 5

Compositions of microemulsions according to the invention with a low fragrance load (using different fragrances) + temperature limits (° C.)

| Composition | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Primary surfactant (w %) Tergitol 15-S-9[1] | 0.05 | 0.05 | 0.05 | 0.05 | 0.075 | 0.075 | 0.125 | 0.125 | 0.125 | 0.125 | 0.09 | 0.09 | 0.125 | 0.125 |
| Primary surfactant (w %) Tergitol 15-S-12[2] | 0.45 | 0.45 | 0.45 | 0.45 | 0.175 | 0.175 | 0.125 | 0.125 | 0.125 | 0.125 | 0.16 | 0.16 | 0.125 | 0.125 |
| First co-surfactant (w %) Solubilizer LRI[3] | 0.3 | 0.3 | 0.3 | 0.3 | 0.15 | 0.15 | 0.15 | 0.15 | 0.025 | 0.025 | 0.025 | 0.025 | 0.15 | 0.15 |
| Second co-surfactant (w %) Tagat CH60[4] | 0.2 | 0.2 | 0.2 | 0.2 | 0.1 | 0.1 | 0.1 | 0.1 | 0.225 | 0.225 | 0.225 | 0.225 | 0.1 | 0.1 |
| total surfactant system (TSS) | 1 | 1 | 1 | 1 | 0.5 | 0.5 | 0.5 | 0.5 | 0.5 | 0.5 | 0.5 | 0.5 | 0.5 | 0.5 |
| Oil phase load fragrance % | 1 | 1 | 1 | 1 | 0.5 | 0.5 | 0.5 | 0.5 | 0.5 | 0.5 | 0.5 | 0.5 | 0.5 | 0.5 |
| ratio Oil phase/TSS | 1 | 1 | 1 | 1 | 1 | 1 | 1 | 1 | 1 | 1 | 1 | 1 | 1 | 1 |
| Oil phase Fragrance | F3 | F4 | F3 | F4 | F3 | F4 | F3 | F4 | F3 | F4 | F3 | F4 | F3 | F4 |
| Co-solvent % iPrOH[5] | 0 | 0 | 3 | 3 | 0 | 0 | 3 | 3 | 0 | 0 | 0 | 0 | 8 | 8 |

TABLE 5-continued

Compositions of microemulsions according to the invention with a low
fragrance load (using different fragrances) + temperature limits (° C.)

| Composition | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Co-solvent % EtOH[6] | 0 | 0 | 0 | 0 | 0 | 0 | 0 | 0 | 2 | 2 | 0.5 | 0.5 | 0 | 0 |
| Upper T limit [° C.] | 42.6 | 45 | 46 | 46.7 | 40.2 | 43.1 | 40.7 | 43.1 | 41.6 | 43.5 | 40.6 | 45.1 | 50.2 | 48.9 |
| Lower T limit [° C.] | <3 | <3 | <3 | <3 | <3 | <3 | <3 | <3 | <3 | <3 | <3 | <3 | <3 | <3 |

[1] PEG(9) secondary alcohol ethoxylate; Origin: Dow Chemicals
[2] PEG(12) secondary alcohol ethoxylate; Origin: Dow Chemicals
[3] Blend of PPG-26 Buteth-26 and PEG(40) hydrogenated castor oil; Origin: LCW Sensient Cosmetic Technologies
[4] PEG(60)Hydrogenated Castor Oil; Origin: Degussa
[5] Isopropyl alcohol; Origin Carlo Erba Reagents
[6] Ethanol; Origin Carlo Erba Reagents

TABLE 6

Compositions of microemulsions according to the invention with a high fragrance load
(using different fragrances and co-solvents) + temperature limits (° C.)

| | Compositions | 15 | 16 | 17 | 18 | 19 | 20 | 21 | 22 | 23 | 24 | 25 | 26 | 27 |
|---|---|---|---|---|---|---|---|---|---|---|---|---|---|---|
| Primary surfactants (w %) | Tergitol 15-S-9[1] | 3.6 | 2.7 | 3.6 | 2.7 | 3.6 | 3.6 | 3.42 | 3.42 | 3.42 | 3.42 | 3.42 | 1.8 | 1.6 |
| | Tergitol 15-S-12[2] | 6.4 | 4.8 | 6.4 | 4.8 | 6.4 | 6.4 | 6.08 | 6.08 | 6.08 | 6.08 | 6.08 | 3.2 | 2.9 |
| First co-surfactant (w %) | Solubilizer LRI[3] | 1 | 0.75 | 1 | 0.75 | 1 | 1 | 0.95 | 0.95 | 0.95 | 0.95 | 0.95 | 0.5 | 0.45 |
| Second co-surfactant (w %) | Tagat CH60[4] | 9 | 6.75 | 9 | 6.75 | 9 | 9 | 8.55 | 8.55 | 8.55 | 8.55 | 8.55 | 4.0 | 3.6 |
| Additional surfactant | Lecithin[9] | 0 | 0 | 0 | 0 | 0 | 0 | 0 | 0 | 0 | 0 | 0 | 0.5 | 0.45 |
| | total surfactant system (TSS) | 20 | 15 | 20 | 15 | 20 | 20 | 19 | 19 | 19 | 19 | 19 | 10 | 9 |
| Oil phase load | fragrance % | 20 | 15 | 20 | 15 | 20 | 20 | 20 | 20 | 20 | 20 | 20 | 10 | 10 |
| | ratio oil phase/TSS | 1 | 1 | 1 | 1 | 1 | 1 | 1.05 | 1.05 | 1.05 | 1.05 | 1.05 | 1 | 1.1 |
| Oil phase | fragrance | F1 | F1 | F3 | F3 | F4 | F2 | F2 | F2 | F2 | F2 | F2 | F4 | F4 |
| Co-solvent | PG[5] (%) | 20 | 15 | 20 | 15 | 20 | 20 | | | | | | 2 | 2 |
| | DIPG[6] (%) | | | | | | | 20 | | | | | | |
| | Ethanol[7] (%) | | | | | | | | 15 | 20 | | | 12 | 15 |
| | Augeo ™ clean multi[8] | | | | | | | | | | 15 | 20 | | |
| | Upper T limit [° C.] | 51.7 | 43.1 | 60 | 54.6 | 60 | 60 | 60 | 60 | 60 | 60 | 57.3 | 44.4 | 40.0 |
| | Lower T limit [° C.] | 3 | 3 | 3 | 3.8 | 3 | 3 | 3 | 3 | 3 | 8.1 | 3 | 3.8 | 4.3 |

[1] PEG(9) secondary alcohol ethoxylate; Origin: Dow Chemicals
[2] PEG(12) secondary alcohol ethoxylate; Origin: Dow Chemicals
[3] Blend of PPG-26 Buteth-26 and PEG(40) hydrogenated castor oil; Origin: LCW Sensient Cosmetic Technologies
[4] PEG(60) Hydrogenated Castor Oil; Origin: Degussa
[5] Propylene glycol; Origin Carlo Erba Reagents
[6] Di-Propylene glycol; Origin Carlo Erba Reagents
[7] Ethanol; Origin Carlo Erba Reagents
[8] Di-Isopropylidene Glycerol; Origin: Rhodia Solvay group
[9] PC 100, phosphatidylcholine One can conclude from these results that microemulsions according to the invention having a low fragrance load or having a high fragrance load present a wide temperature range of transparency. This underlines a good stability over a large oil phase concentration range.

Comparative Example 2

Stability Over a Large Temperature Range

Microemulsions according to the invention and comparative microemulsions were prepared according to the protocol defined in section I.

Comparative microemulsion does not contain a mixture comprising a combination of a first PEG-modified hydrogenated castor oil having more than 19 PEG units with a polypropoxylated-polyethoxylated alcohol (i.e LRI in this example (PPG-26 Buteth-26 and PEG-40 hydrogenated castor oil; Origin: LCW Sensient Cosmetic Technologies) as a first co-surfactant or does not comprise a second co-surfactant. By contrast, microemulsion compositions of the invention still contain LRI as a first co-surfactant and a second co-surfactant (see table 7).

TABLE 7

Composition of microemulsions with transmittance results (T %)

| Composition (% wt) | A | Comparative B | Comparative C |
|---|---|---|---|
| Primary surfactant Tergitol 15-S-9 [1] | 0.5 | 0.5 | 0.5 |
| First co-surfactant Solubilizer LRI [2] | 0.3 | 0.5 | 0 |

TABLE 7-continued

| | Transmittance (%) | Transmittance (%) | Transmittance (%) |
|---|---|---|---|
| Second co-surfactant Tagat CH60 [3] | 0.2 | 0 | 0.5 |
| total surfactant system | 1 | 1 | 1 |
| Oil phase Fragrance F4 | 1 | 1 | 1 |
| ratio oil phase/surfactant system | 1 | 1 | 1 |

| temperature (° C.) | Transmittance (%) | Transmittance (%) | Transmittance (%) |
|---|---|---|---|
| 3 | 97 | 86 | 20 |
| 10 | 100 | 87 | 25 |
| 15 | 100 | 87 | 30 |
| 20 | 100 | 98 | 34 |
| 25 | 100 | 100 | 37 |
| 30 | 100 | 100 | 40 |
| 35 | 100 | 100 | 40 |

[1] PEG(9) secondary alcohol ethoxylate; Origin: Dow Chemicals
[2] Blend of PPG-26 Buteth-26 and PEG(40) hydrogenated castor oil; Origin: LCW Sensient Cosmetic Technologies
[3] PEG-60 Hydrogenated Castor Oil; Origin: Degussa Composition A shows higher stability at high and low temperatures (transmittance=100%) and a wider temperature stability range than comparative compositions B and C.

Comparative Example 3

Microemulsion Compositions Using Different Surfactant Systems

Microemulsions comprising different surfactant systems were prepared (see table 8 below).

These results underline that in any case the usage of a combination of a first and a second co-surfactant synergistically increases the temperature stability of microemulsions compared to systems using either the first or the second co-surfactant alone.

Comparative Example 4

Stability Over a Large Fragrance Concentration Range

Microemulsions were prepared according to formulas of Examples 5C, 5D and 8D of EP 0 571 677 using fragrance F1. Concentrated fragrance/surfactant compositions according to Examples 8D were prepared and diluted. The stability at room temperature is compared for formulas containing between 30% and 0.5% oil phase.

Results are given in table 9 below.

TABLE 9

Composition of microemulsions with transmittance results (T %)

| Compositions | | M | Comparative N | Comparative O |
|---|---|---|---|---|
| | | | Example 5C of EP 0 571 677 | Example 5D/8D EP 0 571 677 |
| Primary surfactants | Tergitol 15-S-7 [1] | 0 | 14 | 14.2 |
| | Tergitol 15-S-9 [2] | 12.5 | 30 | 21.3 |
| | Tergitol 15-S-12 [3] | 12.5 | 5 | 4.5 |
| First co-surfactant | Solubilizer LRI [4] | 15 | 0 | 0 |
| Second co-surfactants | Tagat CH60 [5] | 10 | 0 | 0 |

TABLE 8

Composition of microemulsions with temperature limits (° C.)

| | Composition | Comp. D | Comp. E | F | Comp. G | Comp. H | I | Comp. J | K | Comp. L | M |
|---|---|---|---|---|---|---|---|---|---|---|---|
| Primary surfactants | Tergitol 15-S-9[1] | 0.25 | 0.25 | 0.25 | 0.25 | 0.25 | 0.25 | 0.25 | 0.25 | 0.25 | 0.25 |
| | Tergitol 15-S-12[2] | 0.25 | 0.25 | 0.25 | 0.25 | 0.25 | 0.25 | 0.25 | 0.25 | 0.25 | 0.25 |
| First co-surfactant | Solubilizer LRI[3] | 0.5 | 0 | 0.25 | 0.5 | 0 | 0.25 | 0 | 0.25 | 0 | 0.25 |
| Second co-surfactant | Cremophor RH40[4] | 0 | 0.5 | 0.25 | 0 | 0.5 | 0.25 | 0 | 0 | 0 | 0 |
| | Tagat CH60[5] | 0 | 0 | 0 | 0 | 0 | 0 | 0.5 | 0.25 | 0 | 0 |
| | Tergitol 15-S-30[6] | 0 | 0 | 0 | 0 | 0 | 0 | 0 | 0 | 0.5 | 0.25 |
| | total surfactant system | 1 | 1 | 1 | 1 | 1 | 1 | 1 | 1 | 1 | 1 |
| Oil phase | Fragrance F4 | 0 | 0 | 0 | 1 | 1 | 1 | 1 | 1 | 1 | 1 |
| | Fragrance F2 | 1 | 1 | 1 | 0 | 0 | 0 | 0 | 0 | 0 | 0 |
| | ratio oil phase/surfactant system | 1 | 1 | 1 | 1 | 1 | 1 | 1 | 1 | 1 | 1 |
| | Upper T° limit [° C.] | 39 | not stable | 40 | 39.8 | 39.9 | 39.4 | 38.5 | 40.8 | not stable | 41.7 |
| | Lower T° limit [° C.] | 27.3 | not stable | <3 | 14.9 | 15 | <3 | 19 | <3 | not stable | 12 |

1) PEG(9) secondary alcohol ethoxylate; Origin: Dow Chemicals
2) PEG(12) secondary alcohol ethoxylate; Origin: Dow Chemicals
3) Blend of PPG-26 Buteth-26 and PEG(40) hydrogenated castor oil; Origin: LCW Sensient Cosmetic Technologies
4) PEG(40) Hydrogenated Castor Oil; Origin: BASF
5) PEG(60) Hydrogenated Castor Oil; Origin: Degussa
6) PEG(30) secondary alcohol ethoxylate; Origin: Dow Chemicals TABLE 9-continued

| | | | | |
|---|---|---|---|---|
| Other surfactants | Ucon Lubricant 50-HB 2000 [6] | 0 | 0 | 9 |
| | Aerosol OT [7] | 0 | 1 | 1 |
| Oil phase | Fragance F1 | 50 | 50 | 50 |

| | Dilutions | | |
|---|---|---|---|
| % F1 | T (%) @ 22° C. | T (%) @ 22° C. | T (%) @ 22° C. |
| 30 | 100 | 100 | 100 |
| 20 | 100 | 100 | 100 |
| 10 | 100 | 0 | 0 |
| 5 | 100 | 0 | 0 |
| 2 | 100 | 84 | 0 |
| 1 | 100 | 78 | 70 |
| 0.5 | 100 | 100 | 75 |

[1] PEG(7) secondary alcohol ethoxylate; Origin: Dow Chemicals
[2] PEG(9) secondary alcohol ethoxylate; Origin: Dow Chemicals
[3] PEG(12) secondary alcohol ethoxylate; Origin: Dow Chemicals
[4] Blend of PPG-26 Buteth-26 and PEG(40) hydrogenated castor oil; Origin: LCW Sensient Cosmetic Technologies
[5] PEG(60) Hydrogenated Castor Oil; Origin: Degussa
[6] Propylene oxide ethylene oxide polymer monobutyl ester; Origin Dow Chemicals
[7] Sodium dioctylsulphosuccinate, Origin: Alfa Aesar The above results show that microemulsion of the present invention is stable along the dilution line, whereas comparative microemulsions show high instability at medium oil concentration.

Example 5

Air-Freshener Formulation Comprising the Composition of the Invention (Aerosol)

The following air-freshener formulation was prepared.

Table 10

| air-freshener formulation | |
|---|---|
| Tergitol 15S9 [1] | 0.09 |
| Tergitol 15S12 [2] | 0.16 |
| Tagat CH60 [3] | 0.225 |
| Solubilizer LRI [4] | 0.025 |
| PG [5] | 0.5 |
| Fragrance F4 | 0.5 |
| 2-Methyl-4-isothiazolin-3-one [6] | 0.1 |
| Citric acid [7] | 0.15 |
| Trisodium citrate [8] | 0.38 |
| Inert gas propellant | 0.7 |
| Water | 97.17 |
| Upper T° limit [° C.] | 45.1 |
| Lower T° limit [° C.] | 3 |

[1] PEG(9) secondary alcohol ethoxylate; Origin: Dow Chemicals
[2] PEG(12) secondary alcohol ethoxylate; Origin: Dow Chemicals
[3] PEG(60) Hydrogenated Castor Oil; Origin: Degussa
[4] Blend of PPG-26 Buteth-26 and PEG(40) hydrogenated castor oil; Origin: LCW Sensient Cosmetic Technologies
[5] Propylene glycol; Origin Carlo Erba Reagents
[6] Preservative; Origin: Aldrich
[7] pH regulator; Origin: Acros
[8] pH regulator; Origin: Fluka

The invention claimed is:

1. A microemulsion comprising:
   an oil phase comprising a hydrophobic active ingredient;
   an aqueous phase; and
   a surfactant system comprising:
      a non-ionic primary surfactant system;
      a first non-ionic co-surfactant system, and
      a second non-ionic co-surfactant system;
   characterized in that:
      the non-ionic primary surfactant system comprises at least one ethoxylated alcohol having between 5 and 19 PEG units;
      the first non-ionic co-surfactant system comprises a PEG-modified hydrogenated castor oil having more than 19 PEG units and a polypropoxylated-polyethoxylated alcohol;
      - the second non-ionic co-surfactant system is selected from the group consisting of ethoxylated alcohols having more than 19 PEG units, a PEG-modified hydrogenated castor oil having more than 19 PEG and mixtures thereof, and
   wherein the surfactant system is free from a cationic surfactant and/or anionic surfactant, and
   wherein the microemulsion is stable within the entire temperature range between 12° C. and 35° C.

2. The microemulsion according to claim 1, wherein the weight ratio Rw between the hydrophobic active ingredient and the surfactant system satisfies the following equation, $0.7 \leq Rw \leq 2$.

3. The microemulsion according to claim 1, wherein the non-ionic primary surfactant has an HLB between 9 and 18.

4. The microemulsion according to claim 1, wherein the alkyl group of the ethoxylated alcohol(s) included in the surfactant system is chosen from the group consisting of linear, branched, primary, and secondary alcohols with a chain length containing a total number of carbon atoms between 8 and 18.

5. The microemulsion according to claim 1, wherein the first co-surfactant system comprises PPG-26 Buteth-26 and a PEG-modified hydrogenated castor oil having 40 PEG units.

6. The microemulsion according to claim 1, wherein the second non-ionic co-surfactant system comprises a non-ionic surfactant selected from the group consisting of ethoxylated alcohols having between 20 and 60 PEG units and PEG-modified hydrogenated castor oil having between 20 and 60 PEG units and mixtures thereof.

7. The microemulsion according to claims 5, wherein:
   the first co-surfactant system comprises PPG-26 Buteth-26 and a PEG-modified hydrogenated castor oil having 40 PEG units, and
   the second co-surfactant system comprises a non-ionic surfactant chosen in the group consisting of a PEG-modified hydrogenated castor oil having 30 PEG units, 40 PEG units, 60 PEG units, and mixtures thereof.

8. The microemulsion according to claim 1, wherein the PEG-modified hydrogenated castor oil having more than 19 PEG units comprised in the first non-ionic co-surfactant system is different from the PEG-modified hydrogenated castor oil having more than 19 PEG units comprised in the second non-ionic co-surfactant system.

9. The microemulsion according to claim 1, wherein the microemulsion further comprises a water miscible organic co-solvent.

10. A perfuming composition comprising a microemulsion as defined in claim 1, at least one ingredient selected from the group consisting of a perfuming co-ingredient, a perfumery carrier and mixtures thereof, and optionally at least one perfumery adjuvant.

11. A consumer product comprising the microemulsion as defined in claim 1.

12. The consumer product according to claim 11 in the form of a home cleaning product, a home fragrancing product, a pest control product or a shoe care product.

13. The consumer product according to claim 12, in the form of an air freshener.

14. The consumer product according to claim 11 in the form of a fine fragrance product, a personal care product or an oral care product.

15. A consumer product comprising the perfuming composition as defined in claim 10.

16. The microemulsion according to claim 1, wherein the hydrophobic active ingredient comprises a perfume.

17. The microemulsion according to claim 1, wherein the weight ratio Rw between the hydrophobic active ingredient and the surfactant system satisfies the following equation, $1 \leq Rw \leq 2$.

18. The microemulsion according to claim 1, wherein the non-ionic primary surfactant has an HLB between 10 and 15.

19. The microemulsion according to claim 1, wherein the microemulsion further comprises a water miscible organic co-solvent chosen from the group consisting of mono- and polyhydric solvents and mixtures thereof.

\* \* \* \* \*